United States Patent
Maschke

(10) Patent No.: US 8,231,516 B2
(45) Date of Patent: Jul. 31, 2012

(54) DEVICE FOR APPLYING AND MONITORING OF ENDOVASCULAR BRACHYTHERAPY

(75) Inventor: Michael Maschke, Lonnerstadt (DE)

(73) Assignee: Siemens Aktiengesellschaft, München (DE)

( * ) Notice: Subject to any disclaimer, the term of this patent is extended or adjusted under 35 U.S.C. 154(b) by 1350 days.

(21) Appl. No.: 11/055,869

(22) Filed: Feb. 11, 2005

(65) Prior Publication Data

US 2005/0187422 A1 Aug. 25, 2005

(30) Foreign Application Priority Data

Feb. 20, 2004 (DE) .......................... 10 2004 008 373

(51) Int. Cl.
*A61N 5/00* (2006.01)
*A61N 5/10* (2006.01)

(52) U.S. Cl. .......................................................... 600/1

(58) Field of Classification Search .................. 600/1–8; 378/65; *A61N 5/00, 5/02, 5/10*
See application file for complete search history.

(56) References Cited

U.S. PATENT DOCUMENTS

| | | | | |
|---|---|---|---|---|
| 3,674,014 A | * | 7/1972 | Tillander | 600/434 |
| 3,683,183 A | * | 8/1972 | Vizzini et al. | 250/437 |
| 4,998,932 A | * | 3/1991 | Rosen et al. | 606/29 |
| 5,027,818 A | * | 7/1991 | Bova et al. | 600/427 |
| 5,342,283 A | * | 8/1994 | Good | 600/8 |
| 5,444,254 A | * | 8/1995 | Thomson | 250/370.07 |
| 5,827,313 A | * | 10/1998 | Ream | 606/171 |
| 5,899,882 A | * | 5/1999 | Waksman et al. | 604/103.07 |
| 6,033,357 A | | 3/2000 | Ciezki et al. | |
| 6,069,698 A | * | 5/2000 | Ozawa et al. | 356/511 |
| 6,077,213 A | | 6/2000 | Ciezki et al. | |
| 6,175,655 B1 | * | 1/2001 | George et al. | 382/257 |
| 6,222,544 B1 | * | 4/2001 | Tarr et al. | 715/839 |
| 6,241,670 B1 | * | 6/2001 | Nambu | 600/427 |
| 6,494,835 B1 | | 12/2002 | Ciezki et al. | |
| 6,561,966 B1 | | 5/2003 | Smith et al. | |
| 7,322,929 B2 | * | 1/2008 | Lovoi | 600/3 |
| 2001/0027261 A1 | * | 10/2001 | Ciezki et al. | 600/3 |
| 2001/0056219 A1 | * | 12/2001 | Brauckman et al. | 600/3 |
| 2003/0125752 A1 | | 7/2003 | Werp et al. | |
| 2003/0236443 A1 | * | 12/2003 | Cespedes et al. | 600/29 |
| 2004/0186368 A1 | * | 9/2004 | Ramzipoor et al. | 600/407 |
| 2005/0096647 A1 | * | 5/2005 | Steinke et al. | 606/41 |
| 2005/0111621 A1 | * | 5/2005 | Riker et al. | 378/65 |
| 2005/0171436 A1 | * | 8/2005 | Clarke et al. | 600/476 |

(Continued)

FOREIGN PATENT DOCUMENTS

EP 0 885 594 A2 12/1998

(Continued)

OTHER PUBLICATIONS

W.A. Wohlgemuth, K. Bohndorf, "Endovascular Brachytherapy to Prevent Restenosis after Angioplasty", Fortschr Röntgenstr 2003: 175: pp. 246-252.

*Primary Examiner* — Charles A. Marmor, II
*Assistant Examiner* — Catherine E Burk

(57) ABSTRACT

Device for implementing endovascular brachytherapy, whereby in the region of the catheter tip, a beta or gamma radiator used to prevent restenosis after the removal of plaque from vessel walls emits radioactive radiation in order to suppress the structural vessel alteration, with simultaneous OCT-monitoring, whereby a brachytherapy is combined with an OCT catheter in an integrated unit.

13 Claims, 2 Drawing Sheets

U.S. PATENT DOCUMENTS

| | | | |
|---|---|---|---|
| 2006/0015126 A1* | 1/2006 | Sher | 606/159 |
| 2007/0270635 A1* | 11/2007 | Schellenberg | 600/101 |
| 2008/0071215 A1* | 3/2008 | Woods et al. | 604/116 |
| 2010/0174234 A1 | 7/2010 | Werp et al. | |

FOREIGN PATENT DOCUMENTS

| | | |
|---|---|---|
| JP | 02185269 A | 7/1990 |
| JP | 03218775 A | 9/1991 |
| JP | 10277169 A | 10/1998 |
| JP | 2001112876 A | 4/2001 |
| JP | 2001190700 A | 7/2001 |
| JP | 2001514040 A | 9/2001 |
| JP | 2002113017 A | 4/2002 |
| JP | 2002214127 A | 7/2002 |
| WO | WO 97/25102 | 7/1997 |
| WO | WO 01/11409 A2 | 2/2001 |

* cited by examiner

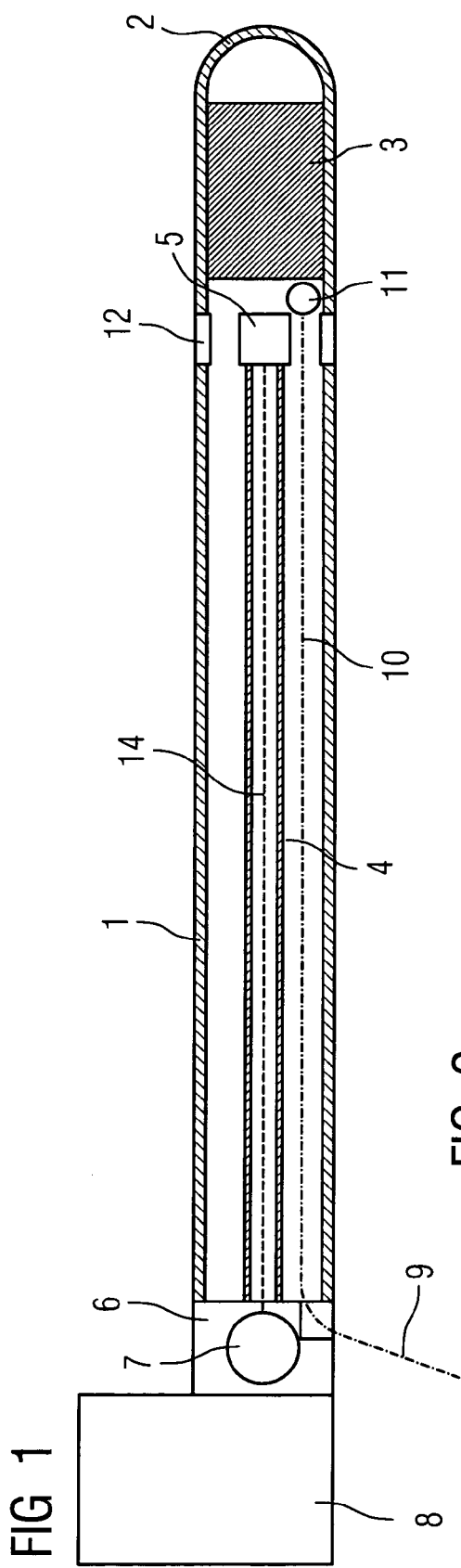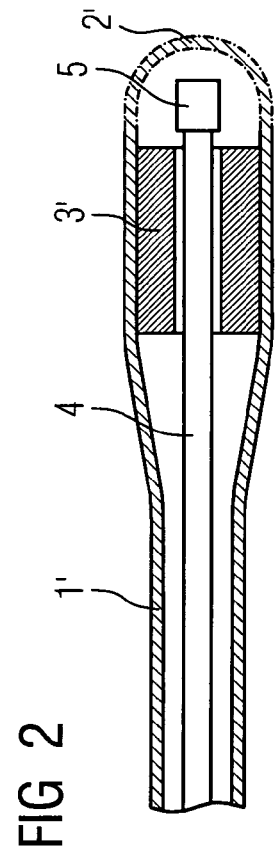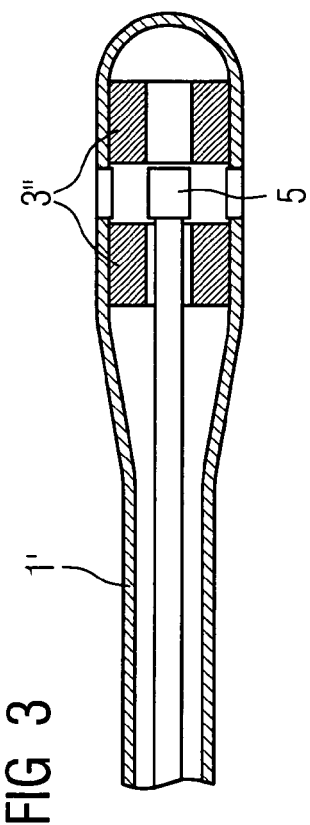

DEVICE FOR APPLYING AND MONITORING OF ENDOVASCULAR BRACHYTHERAPY

CROSS REFERENCE TO RELATED APPLICATIONS

This application claims priority to the German application No. 10 2004 008 373.8, filed Feb. 20, 2004 which is incorporated by reference herein in its entirety.

FIELD OF INVENTION

The invention relates to a device for implementing endovascular brachytherapy, whereby in the area of the catheter tip, a beta or gamma radiator used to prevent restenosis after the removal of plaque from vessel walls emits radioactive radiation in order to suppress the structural vessel alteration, with simultaneous OCT-monitoring.

BACKGROUND OF INVENTION

One of the world's most common fatal diseases is vascular disease, in particular heart infarct. This is caused by diseases of the coronary arteries (Arteriosclerosis). Deposits (arteriosclerotic plaque) result in a 'blockage' in the coronary arteries.

If the coronary angiography shows serious narrowing (Stenosis) in the coronary arteries, which cause angina pectoris, restrict a person's performance and/or pose a threat to the life of the patient, then a PTCA (percutaneous transiluminal coronary angioplasty) is nowadays carried out in the majority of cases. During this the constrictions in the coronary arteries are widened using a so-called balloon catheter.

Clinical studies have shown that with many patients, this method results in restenosis, sometimes up to 50% of patients show restenosis. The use of stents positioned in the widened constrictions can reduce the restenosis rate by up to 25%.

Endovascular brachytherapy can further reduce restenosis, the method was first licensed in 2000 by the FDA (Food and Drug Administration) for a beta and a gamma-radiator. The advance of the causal arteriosclerosis and the response of the vessel wall to the PCTA-induced trauma are causes for post-interventional restenosis. The stent implantation prevents a structural vessel alteration by means of the mechanical restoring force of the stent, but nevertheless stimulates the neointima hyperplasia. In contrast, after a single PTCA the structural vessel alteration predominates during the onset of restenosis.

Clinical studies have shown that the endovascular radiation reduces the restenosis. The mechanisms have still not be fully clarified, nevertheless different models are discussed, e.g. cell death, cell inactivation, hindrance in the cell migration, suppression of the structural vessel alteration and blockage of the extra cellular matrix synthesis.

The radioactivity can either be applied by means of catheter-based radioactive wires or seeds, or administered as radioactive fluids directly by means of a PTCA balloon. Previous experience has shown that the concept of the radioactively loaded stents unfortunately shows a high restenosis rate. The wire-based systems stand out as the most favorable solution. With wire-based systems, the radiation source is applied to the tip of a wire which is then manually moved into the target position by means of a mechanical after-loading device. One problem of this technique is the possibly eccentric position of the wire in the vessel volume. This results in an overdosage on the vessel wall side near to the wire and an underdosage on the vessel wall side away from the wire.

For centering of the radioactive wire in the vessel lumen segmented and helical balloons are fitted to the applicator around the wire, which should guarantee an improved homogeneity of the radiation dose. [Wohlgemut W A, Bohndorf K Endovasculäre Brachytherapie in der Restenoseprophylaxe nach Angioplastie und Stentimplantation, Fortsch. Röntgenstr. 2003; 175; 246-252]. (Endovascular Brachytherapy in the restenosis prophylax after angioplasty and stent implantation).

SUMMARY OF INVENTION

These solutions are nevertheless also based on the theoretical assumption that the two-dimensional image of the vessel shown in the angiography using contrast means displays a completely symmetrical tube, the deposits therein being evenly distributed on the periphery.

A device for intravascular brachytherapy is described in WO 97/25102 for example.

Clinical studies using the insertion of a IVUS catheter (Intravascular Ultrasound) into the vessel improve the imaging information, but are nevertheless disadvantageous in that a relatively expensive catheter must additionally be inserted into the patient. Furthermore, the spacial resolution of IVUS is not particularly good. An IVUS system is described in DE 198 27 460 A1 for instance.

U.S. Pat. No. 6,494,835 discloses a device which combines a wire-based brachytherapy system with an IVUS probe, but this solution also has the disadvantage of a low special resolution of IVUS.

An object of the invention is thus to create a device for applying endovascular brachytherapy using simultaneous OCT monitoring thus avoiding the exchange of different catheters.

This object is achieved by the claims combining a brachytherapy catheter with an OCT catheter into an integrated unit.

This thereby results in a reduction in the method steps and a reduction in the catheters used. The images of the OCT-system, as disclosed in WO 01/11409 for example, provide important additional medical information about the deposits (arteriosclerotic plaque), for instance, inflammatory processes to achieve the correct position of the brachytherapy radiator in the vessel. The correct position of the radiator is important in order to prevent an overdosage as well as an underdosage on the vessel wall. The advantage of the OCT catheter which can be positioned on the target position at the same time as the brachytherapy catheter is the extremely high detail resolution of structures near to the vessel surface, so that microscopic tissue representations are sometimes possible.

In a further development of the invention, provision can be made for rotating OCT signal lines to be arranged in the flexible, tube-shaped catheter sheath of a brachytherapy catheter, which results in an OCT sensor (rotating mirror) being arranged within a circulating ring window, which is arranged directly in front of or behind the radiator or between distanced segments of a split radiator.

A particularly advantageous embodiment results thereby in that the OCT-signal line preferably designed as a glass fiber line is positioned within a hollow flexible drive shaft for the OCT sensor.

The catheter sheath can be provided in a known manner with end-side inlets or outlets for contrast means or rinsing fluids.

Magnets for magnetic navigation can be arranged on the catheter tip, furthermore the arrangement could be also designed such that it can be slid onto a continuous guide wire, which can be inserted into the target position in vessel even before insertion into the brachytherapy catheter.

Furthermore, it is also possible to arrange a preferably multicavity inflatable balloon onto the catheter tip, said inflatable balloon serving to fix the catheter and/or the vessel dilation.

It is of particular advantage for the brachytherapy catheter to be provided with a ring-shaped or radially offset radiator, and configured such that the OCT catheter can be inserted into the brachytherapy catheter, whereby in the case of a forward opening catheter sheath of the brachytherapy catheter, in this case naturally provided with its own catheter sheath, the OCT catheter can be pushed through the brachytherapy catheter, so that the OCT-probe can be arranged in front of the combined examination/treatment catheter.

The OCT imaging system can be extended by menus in order to enable a quantification of the applied radiation. For instance, isocentric radiation lines can be blended into the OCT image. Additionally the duration of the applied radiation can be measured and coupled to a notification device for discharging optical and/or acoustic warning notifications for the end of the radiation.

Finally, also within the framework of the invention, the user interface includes input possibilities by means of a keyboard and/or barcode for entering the radiation parameters of the probe (dose, activation data, half-life).

BRIEF DESCRIPTION OF THE DRAWINGS

Further advantages, features and details of the invention are set out in the following description of a single exemplary embodiment, and with reference to a schematic drawing, in which;

FIG. 1 shows a section through a brachytherapy OCT catheter according to the invention FIG. 2 shows a section through an adapted catheter with a radiator configured in the shape of a ring for inserting or pushing through the OCT catheter FIG. 3 shows a section through an adapted catheter whereby the radiator is split.

DETAILED DESCRIPTION OF INVENTION

Figure 4:
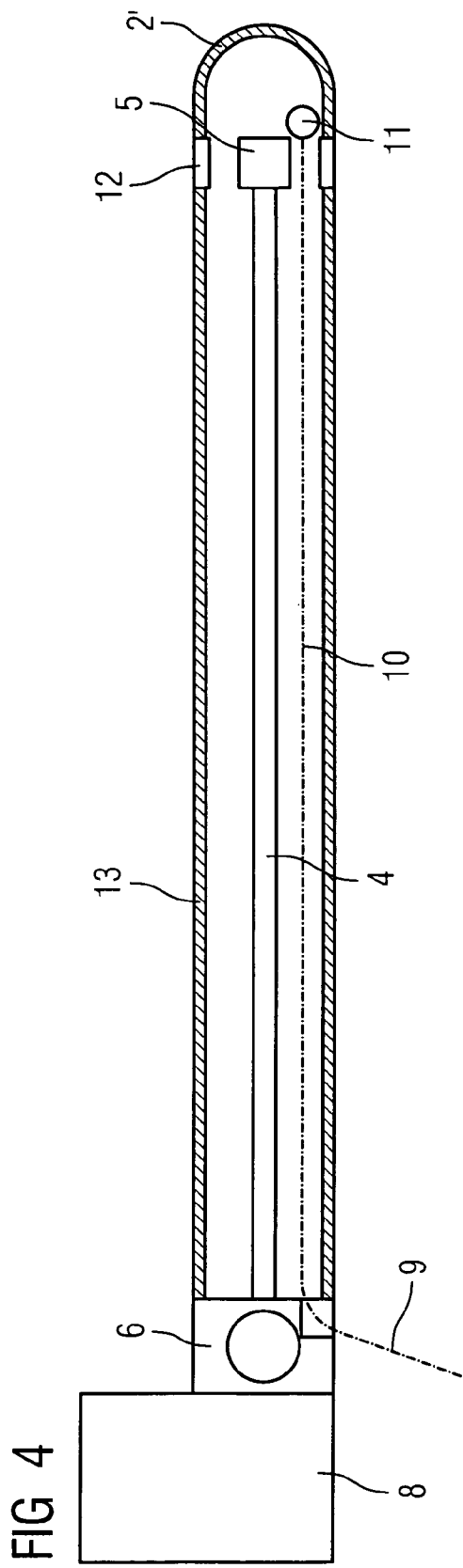
FIG. 4 shows a schematic representation of an OCT catheter with its own catheter sheath for pushing through the forward opening brachytherapy catheter according to FIG. 3, and FIGS. 5 and 6 show OCT-recordings from the vessel with high resolution in the close-up range, whereby isocentric radiation lines are additionally shown in FIG. 6.
Figure 6:
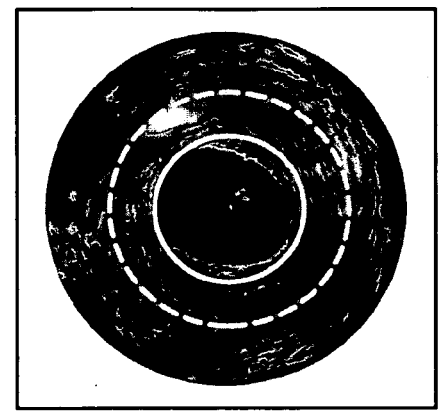
Figure 5:
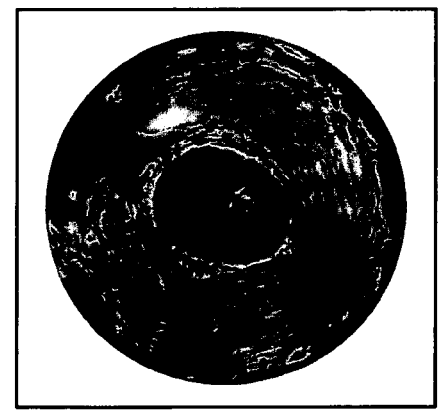

The combined brachytherapy OCT catheter according to FIG. 1 comprises a catheter sheath 1 with a radiator 3 arranged in the region of the rounded catheter tip 2, which can be configured as a beta radiator or also as a gamma radiator, whereby this radiator must not necessarily be designed in a wrap-around radiating manner, but can obviously also be configured such that it deliberately only radiates in one direction, whereby the radiation direction can be precisely adjusted by means of a rotatable diaphragm and/or by a corresponding twisting of the catheter sheath, according to the results achieved with the OCT examination of the inner wall of the vessel.

In addition to the radiator 3, an OCT observation system is also arranged in the catheter sheath 1, which does not need to be designed as a complete catheter with its own catheter sheath as shown in the exemplary embodiment. With 4, a hollow drive shaft can be seen for the OCT sensor 5 configured as a rotatable mirror, whereby the signal lines 14 for the OCT sensor are accommodated in this shaft 4 for the OCT sensor, which can preferably be configured as glass fiber lines. The mechanical connection system is schematically indicated with 6, and a rotational coupling with 7. The signal interface for the drive unit for the OCT is indicated schematically by the small box 8. Finally 9 indicates a connection for a contrast means or a rinsing fluid, which preferably opens out within a individual line 10 within the catheter sheath into an outlet opening 11 in the catheter sheath in the region of the preferably wrap-around window 12 for the OCT sensor 5.

FIG. 2 shows an adapted embodiment of a combined brachytherapy OCT catheter, whereby the radiator 3' is designed in the shape of a ring, so that the OCT catheter can be completely pushed through this radiator 3', so that it lies within the rounded tip 5 of the catheter sheath 1', which of course must be transparent at this position.

The design variant according to FIG. 3 can also be selected instead of the complete pushing through method, whereby the radiator comprises two distanced ring segments 3", between which the OCT sensor 5 is positioned and can radiate outwards.

If necessary, the rounded tip 2 of the catheter sheath of the brachytherapy catheter could also be completely left out in the dashed area in FIG. 2, if a complete OCT-catheter is used in conjunction with this brachytherapy catheter, comprising its own catheter sheath 13, as shown in FIG. 4. A complete OCT catheter of this type according to FIG. 4 (the scales in FIG. 4, and FIGS. 2 and 3 are naturally different) enables a pushing-through of the OCT catheter through the brachytherapy catheter after which this is inserted into the target position in the vessel.

The typical process using a combined brachytherapy OCT catheter according to the invention is as follows; insertion of the catheter using X-ray monitoring, possibly using contrast means, insertion of a rinsing fluid after having achieved the desired target position in order to clean the observation area for the OCT-method and in order to enable an examination of the stenosis with the OCT method at a higher resolution; positioning of the brachytherapy probe based on the image data of the OCT-recording, possibly with the additional help of angiography recordings and withdrawal of the integrated catheter after applying the radiation dose provided.

The invention is not restricted to the exemplary embodiments shown. In addition to the possibility of adapting the insertion technique using a guide wire and/or guide catheter, magnetic navigation can additionally also be provided, whereby permanent magnets or electromagnets are used on the catheter tip and/or on the catheter. Furthermore, an inflatable balloon and a balloon with several cavities can also be applied to the tip in order to position the radiator in the desired axial position and/or to retain it there. Finally it would also be possible to provide the conventional X-ray markers on the catheter shaft, which are not shown in the drawing for the sake of improved clarity.

Furthermore, the use of a brachytherapy OCT catheter according to the invention is not restricted to its use in coronary arteries.

The invention claimed is:

1. A device for applying endovascular brachytherapy, comprising:
   a brachytherapy catheter having a catheter tip;
   a flexible tube-shaped catheter jacket of the brachytherapy catheter;
   an OCT catheter simultaneously used with the brachytherapy catheter that is arranged within the flexible tube-shaped catheter jacket of the brachytherapy catheter and positioned on a target position at the same time as the brachytherapy catheter, the brachytherapy and OCT catheters forming one integrated catheter unit;

a radiation emitter attached to the catheter tip of the brachytherapy catheter and adapted to prevent restenosis after plaque removal from a vascular wall by emitting radioactive radiation;

an OCT image system connected to the OCT catheter; and a control device having a user interface for controlling the device, the user interface including an input device for entering radiation parameters of the radiator, wherein the radiation parameters of the radiation emitter include parameters of activation data and half-life period, wherein the OCT catheter comprises at least one rotating OCT signaling line arranged within the flexible tube-shaped catheter jacket of the brachytherapy catheter, the rotating OCT signaling line connected to a rotating OCT sensor arranged within a circumferential ring-shaped window, the rotating OCT sensor being a rotating mirror, wherein the OCT sensor is arranged within the brachytherapy catheter and adjacent to the radiation emitter, wherein the radiation emitter is a split emitter comprising at least two emitter parts and the OCT sensor is arranged between a first and a second emitter part, wherein the OCT image system is adapted to fade isocentric radiation lines into an OCT image of the OCT image system, and wherein the OCT image system is adapted to measure a duration of applied radiation.

2. The device according to claim 1, wherein the radioactive radiation comprises beta or gamma radiation.

3. The device according to claim 1, wherein the radioactive radiation suppresses a structural vessel alteration.

4. The device according to claim 1, wherein the OCT signaling line are arranged within a hollow, flexible drive shaft of the OCT sensor.

5. The device according to claim 4, wherein the OCT signaling line comprises an optical fiber.

6. The device according to claim 1, wherein the catheter jacket includes an inlet and/or an outlet for feeding and discharging a contrast medium or rinsing fluid to or from the brachytherapy catheter.

7. The device according claim 1, further comprising a plurality of magnets arranged at the catheter tip allowing for a magnetic navigation of the device.

8. The device according to claim 1, further comprising a continuous guide wire.

9. The device according to claim 1, further comprising an inflatable balloon arranged at the catheter tip of the brachytherapy catheter for locating the catheter and/or for performing vessel dilation.

10. The device according to claim 9, wherein the balloon comprises a plurality of inflatable balloon chambers.

11. The device according to claim 1, wherein the brachytherapy catheter comprises a ring-shaped radiator and/or a radially offset arranged radiator relative to a center axis of the brachytherapy catheter allowing for the OCT catheter to be inserted into the brachytherapy catheter.

12. The device according to claim 11, wherein the flexible tube-shaped catheter jacket of the brachytherapy catheter has a forward opening and the OCT catheter includes a second catheter jacket allowing for the OCT catheter to be pushed through the brachytherapy catheter.

13. The device according to claim 1, further comprising an optical and/or acoustic warning device adapted to be triggered by a specified duration of the applied radiation for preventing excessive radiation.

* * * * *